(12) United States Patent
Motai et al.

(10) Patent No.: US 10,709,441 B2
(45) Date of Patent: Jul. 14, 2020

(54) SUTURE BODY AND SUTURE SYSTEM

(71) Applicant: OLYMPUS CORPORATION, Hachioji-shi, Tokyo (JP)

(72) Inventors: Kosuke Motai, Hidaka (JP); Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 261 days.

(21) Appl. No.: 15/896,454

(22) Filed: Feb. 14, 2018

(65) Prior Publication Data

US 2018/0168570 A1 Jun. 21, 2018

Related U.S. Application Data

(63) Continuation of application No. PCT/JP2016/065431, filed on May 25, 2016.

(30) Foreign Application Priority Data

Aug. 20, 2015 (JP) .................. 2015-162452

(51) Int. Cl.
*A61B 17/06* (2006.01)
*A61B 17/04* (2006.01)
(Continued)

(52) U.S. Cl.
CPC .... *A61B 17/06004* (2013.01); *A61B 17/0485* (2013.01); *A61B 17/0487* (2013.01);
(Continued)

(58) Field of Classification Search
CPC ......... A61B 17/04; A61B 17/06; A61B 17/12; A61B 17/06004; A61B 17/0485;
(Continued)

(56) References Cited

U.S. PATENT DOCUMENTS

2007/0213745 A1 9/2007 Takemoto et al.
2009/0182192 A1* 7/2009 Shiono ................... A61B 1/018
600/103
(Continued)

FOREIGN PATENT DOCUMENTS

JP H08-140982 A 6/1996
JP 2007-236679 A 9/2007
(Continued)

OTHER PUBLICATIONS

Jul. 5, 2016 International Search Report issued in International Patent Application No. PCT/JP2016/065431.

*Primary Examiner* — Vi X Nguyen
(74) *Attorney, Agent, or Firm* — Oliff PLC

(57) ABSTRACT

A suture body includes: a suture thread having a first end and a second end and fixed to a living tissue; a suture needle connected to the first end; and a thread fixing member connected to the second end. The thread fixing member includes: a rod-shaped protruding portion; and an elastic member having an outer circumferential surface and arranged so that the thread fixing member is in contact with the outer circumferential surface at a predetermined contact pressure. The suture body is configured so that the suture thread can enter between the protruding portion and the elastic member by elastically deforming the elastic member. The suture body further includes a base body to which the protruding portion and the elastic member are fixed. The protruding portion and the elastic member are arranged in an area surrounded by an outer diameter of the base body.

12 Claims, 6 Drawing Sheets

(51) Int. Cl.
*A61B 17/062* (2006.01)
*A61B 17/12* (2006.01)
*A61B 17/00* (2006.01)

(52) U.S. Cl.
CPC ...... *A61B 17/062* (2013.01); *A61B 17/12009* (2013.01); *A61B 17/0401* (2013.01); *A61B 17/06166* (2013.01); *A61B 2017/0034* (2013.01)

(58) Field of Classification Search
CPC .......... A61B 17/06166; A61B 17/0401; A61B 17/12009; A61B 2017/0409; A61B 2017/0414
See application file for complete search history.

(56) References Cited

U.S. PATENT DOCUMENTS

| | | |
|---|---|---|
| 2011/0098743 A1 | 4/2011 | Lyons et al. |
| 2012/0165865 A1 | 6/2012 | Fujisaki et al. |

FOREIGN PATENT DOCUMENTS

| | | |
|---|---|---|
| JP | 2012-130669 A | 7/2012 |
| JP | 2013-094409 A | 5/2013 |
| JP | 2014-217633 A | 11/2014 |
| WO | 2004/049898 A2 | 6/2004 |
| WO | 2013/065860 A1 | 5/2013 |

\* cited by examiner

US 10,709,441 B2

SUTURE BODY AND SUTURE SYSTEM

CROSS REFERENCE TO RELATED APPLICATIONS

This application is a continuation application based on a PCT Patent Application No. PCT/JP2016/065431, filed on May 25, 2016, whose priority is claimed on Japanese Unexamined Patent Application, First Publication No. 2015-162452, filed on Aug. 20, 2015, the entire contents of which are hereby incorporated by reference.

BACKGROUND OF THE INVENTION

Field of the Invention

The present invention relates to a suture body and a suture system for medical purpose.

Description of the Related Art

Conventionally, various treatments are performed using a flexible endoscope inserted in a luminal organ such as an alimentary canal. Generally, these procedures are performed by inserting a treatment tool for endoscope into a channel provided in an endoscope insertion portion, and protruding the distal end of the treatment tool from the distal end of the endoscope insertion portion.

Suturing using a suture thread is one of difficult procedures. A series of procedures of suturing includes an operation of making the suture thread pass through a tissue and an operation of forming a knot on the suture thread so that the suture thread hung on the tissue keeps applying a predetermined tension to the tissue. The latter is more difficult, and it is not easy to do it with the treatment tool.

It is proposed, instead of forming the knot, to have the distal end of the suture thread hung on the tissue fixed to the thread fixing member attached to the proximal end of the suture thread so as to achieve the same function as forming the knot. (For example, refer to Japanese Unexamined Patent Application, First Publication No. H8-140982.)

SUMMARY

A first aspect of the present invention is a suture body including: a suture thread that has a first end and a second end and is fixed to a living tissue; a suture needle that is connected to the first end; and a thread fixing member that is connected to the second end. The thread fixing member includes: a rod-shaped protruding portion; and an elastic member that has an outer circumferential surface and is arranged so that the thread fixing member is in contact with the outer circumferential surface at a predetermined contact pressure. The suture body is configured so that the suture thread can enter between the protruding portion and the elastic member by elastically deforming the elastic member. The suture body further includes a base body to which the protruding portion and the elastic member are fixed. The protruding portion and the elastic member are arranged in an area surrounded by an outer diameter of the base body.

The protruding portion may be in contact with two or more surfaces of the elastic member at the contact pressure.

The suture thread may extend in a lower side opposite to an upper side where the protruding portion is arranged in the thread fixing member.

The suture body may further include: a plurality of leg portions formed of a flexible material and extending in the lower side.

A second aspect of the present invention is a suture system including: the above suture body; an endoscope having a channel into which the suture body can be inserted; and a sheath configured to be inserted into the channel and having a notch at a distal end thereof.

DETAILED DESCRIPTION OF THE PREFERRED EMBODIMENTS

Figure 1:
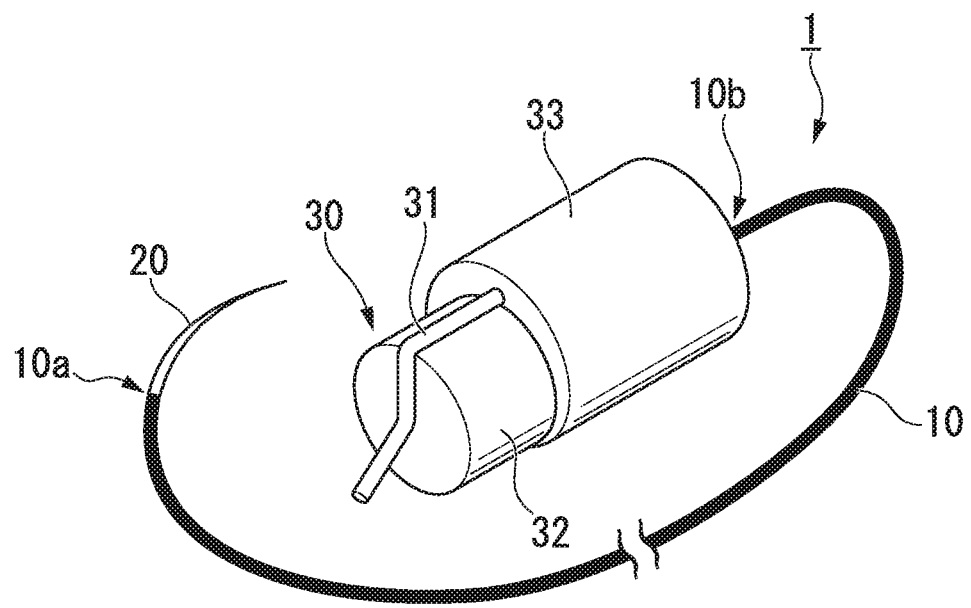
FIG. 1 is a perspective view showing a suture body according to a first embodiment of the present invention.

A first embodiment of the present invention will be described with reference to FIGS. 1 to 8. FIG. 1 is a perspective view showing the suture body 1 of the present embodiment. The suture body 1 includes a suture thread 10, a suture needle 20 connected to a first end 10a of the suture thread 10, and a thread fixing member 30 connected to a second end 10b of the suture thread 10.

There are no particular restrictions on the material, structure, and the like of the suture thread 10 as long as the living tissue can be sutured, and various kinds of known sutures can be appropriately selected and used.

As for the suturing needle 20, a so-called curved needle is exemplified in FIG. 1, but the present invention is not limited to this, and there are no restrictions on the shape, structure and the like as long as the suturing needle can puncture the living tissue. The specific configuration of the suturing needle 20 may be appropriately determined in consideration of the configuration of a suture instrument used when hooking the suture thread 10 to the tissue and the like, i.e., making the suture thread 10 pass through the tissue and the like.

Figure 2:
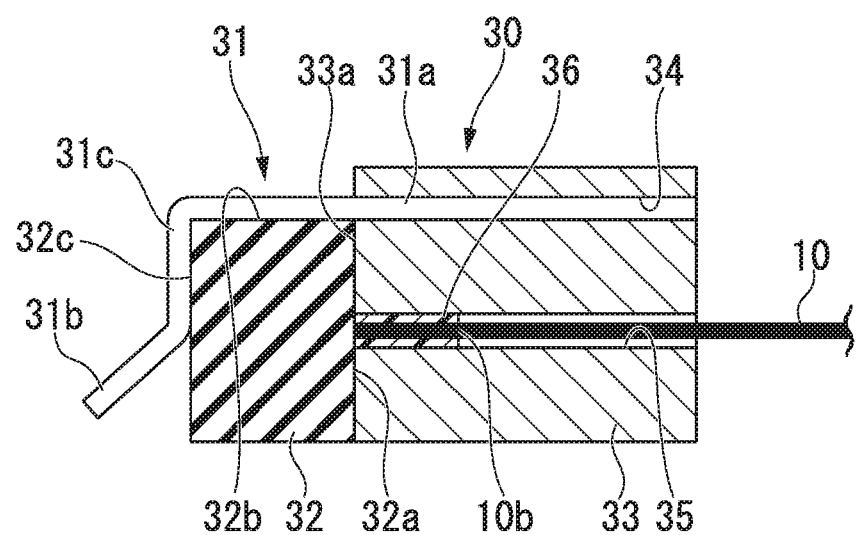
FIG. 2 is a cross-sectional view showing a thread fixing member of a suture body according to the first embodiment of the present invention.

FIG. 2 is a cross-sectional view of the thread fixing member 30. The thread fixing member 30 includes a rod-like protruding portion 31 around which the suture thread 10 is wound and an elastic member 32 arranged to maintain a contact state with the protruding portion 31. Both of the protruding portion 31 and the elastic member 32 are fixed to the base body 33.

The protruding portion 31 is formed in a linear shape or a rod shape with a material having a certain rigidity such as metal or resin. The protrusion 31 has a first region 31a on the proximal side, a second region 31b on the distal side, and an intermediate portion 31c between the first region 31a and the second region 31b. The base end side of the first region 31a enters a first through hole 34 formed in the base body 33 and is fixed to the base body 33.

The elastic member 32 is formed in a cylindrical shape with a material such as rubber or elastomer. The proximal end surface 32a of the elastic member 32 is fixed to the distal end surface 33a of the base body 33 by an adhesion or the like. The first region 31a of the protruding portion 31 is in contact with the outer peripheral surface 32b of the elastic member 32 and the intermediate portion 31c is in contact with the distal end surface 32c of the elastic member 32.

In the outer peripheral surface 32b and the distal end surface 32c, a portion in contact with the protruding portion 31 is pressed and elastically deformed. As a result, the protruding portion 31 and the elastic member 32 maintain a contact state with a constant contact pressure.

The base body 33 is a member formed in a substantially columnar shape with resin, metal or the like. The base body 33 has a first through hole 34 through which the protruding portion 31 is inserted and fixed and a second through hole 35 through which the second end 10b of the suture thread 10 is inserted and fixed. The first through hole 34 is provided at a position close to the outer peripheral surface away from the axis of the base body 33, and the second through hole 35 is provided at a position closer to the axis than the first through hole 34. The second end 10b of the suture thread 10 is fixed in the second through hole 35 by the adhesive 36.

The size of the suture body 1 including the thread fixing member 30 is set so that the suture body as a whole can be inserted through a treatment instrument channel (described later) of the endoscope.

Figure 3:
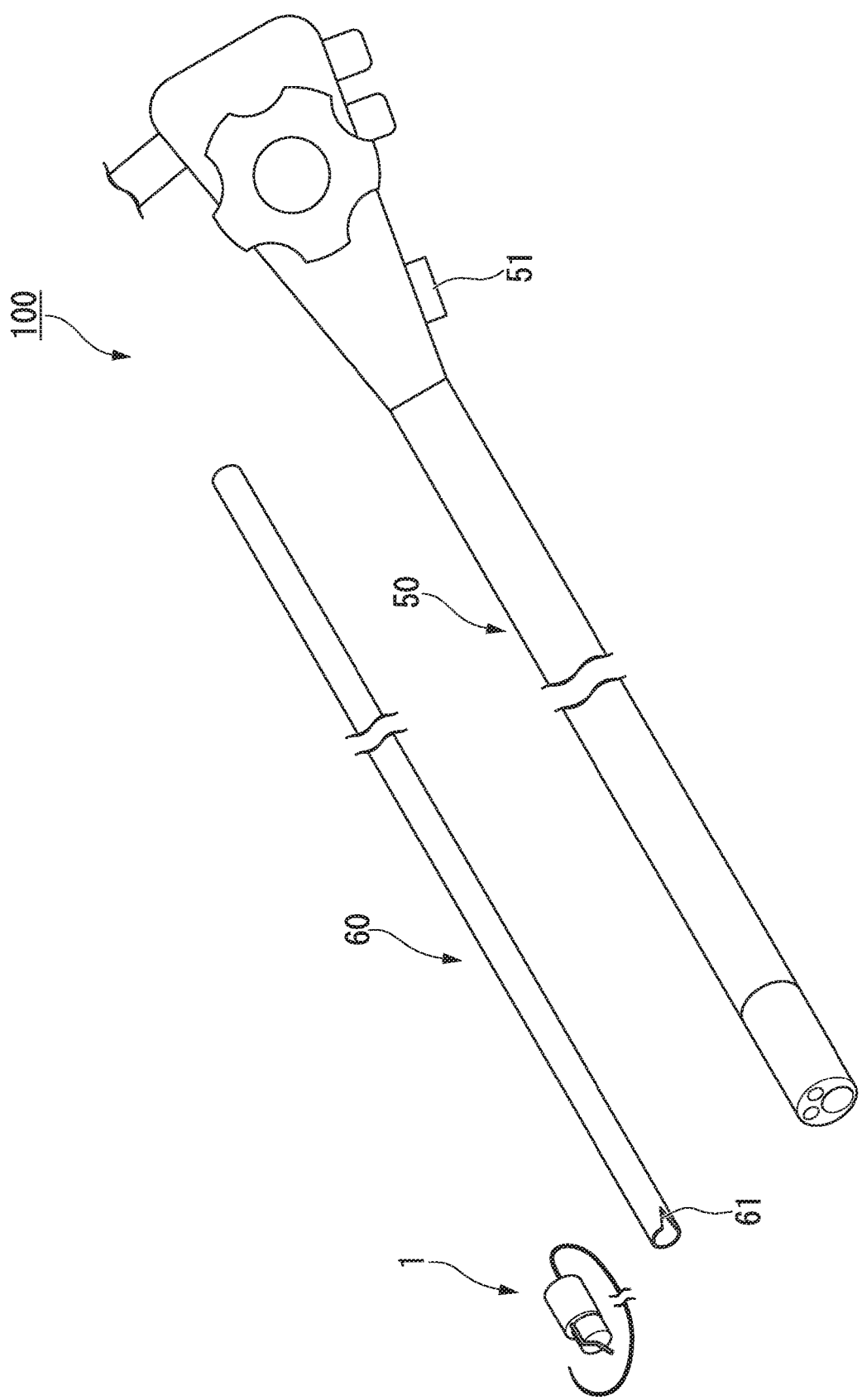
FIG. 3 is a view showing a suture system including a suture body according to the first embodiment of the present invention.

The operation of the suture body 1 configured as described above during use will be described. FIG. 3 shows a suture system 100 of the present embodiment including the suture body 1. The suture system 100 includes a suture body 1, a flexible endoscope 50 into which the suture body 1 is inserted, and a sheath 60 inserted through a treatment instrument channel of the endoscope 50.

First, the surgeon introduces the endoscope 50 into the body of a patient and introduces the distal end portion of the endoscope 50 near the target portion to be sutured. After confirming the object part, the suture needle 20 of the suture body 1 is attached to a commonly-known suture instrument (not shown) that can use the suture needle 20, thereby the suture body 1 is attached to the suture instrument. Then, the suture body 1 and the suture instrument are inserted in this order from the forceps opening 51 to the treatment instrument channel (not shown) of the endoscope 50.

The surgeon advances the suture instrument to protrude the distal end portion of the suture body 1 and the suture instrument from the distal end of the endoscope 50. The surgeon punctures the tissue of the target site with the suture needle 20 using the suture instrument and hooks the suture thread 10 on the tissue (thread hooking process). In the thread hooking process, since the thread fixing member 30 does not enter the tissue of the target site, the thread fixing member functions as an anchor for preventing threads hooked on the tissue from coming off.

In addition, in the thread hooking process, in order to make it easier to perform a thread fixing process to be performed later, it is preferable to adjust the orientation of the thread fixing member 30 so that the proximal end of the thread fixing member 30 is located on the near side of the field of view of the endoscope 50 and the tip of the protruding portion 31 extends toward the back of the visual field.

When the thread hooking process is completed, the surgeon separates the suture needle 20 from the suture thread 10 and removes the suture instrument from the endoscope 50. Next, the sheath 60 is inserted into the forceps opening 51. The sheath 60 is a tubular member formed of resin or the like, and has an inner diameter such that the thread fixing member 30 cannot enter. At the tip portion of the sheath 60, a notch 61 is provided for drawing the grasping forceps that grasps the suture thread 10 to the inside of the sheath in the thread fixing process, which will be described later. Since the sheath 60 is similar to a commonly-known medical sheath except for the notch 61, the sheath can be formed by appropriately fabricating a commonly-known medical sheath.

Figure 4:
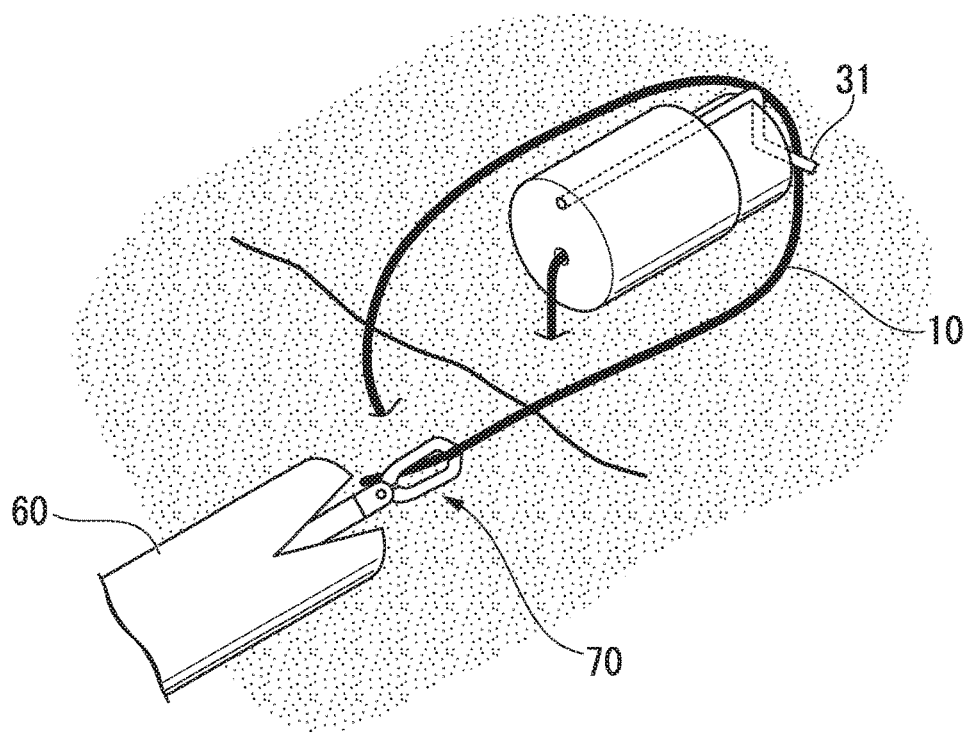
FIG. 4 is a view showing an operation when using the suture system including the suture body according to the first embodiment of the present invention.
Figure 5:
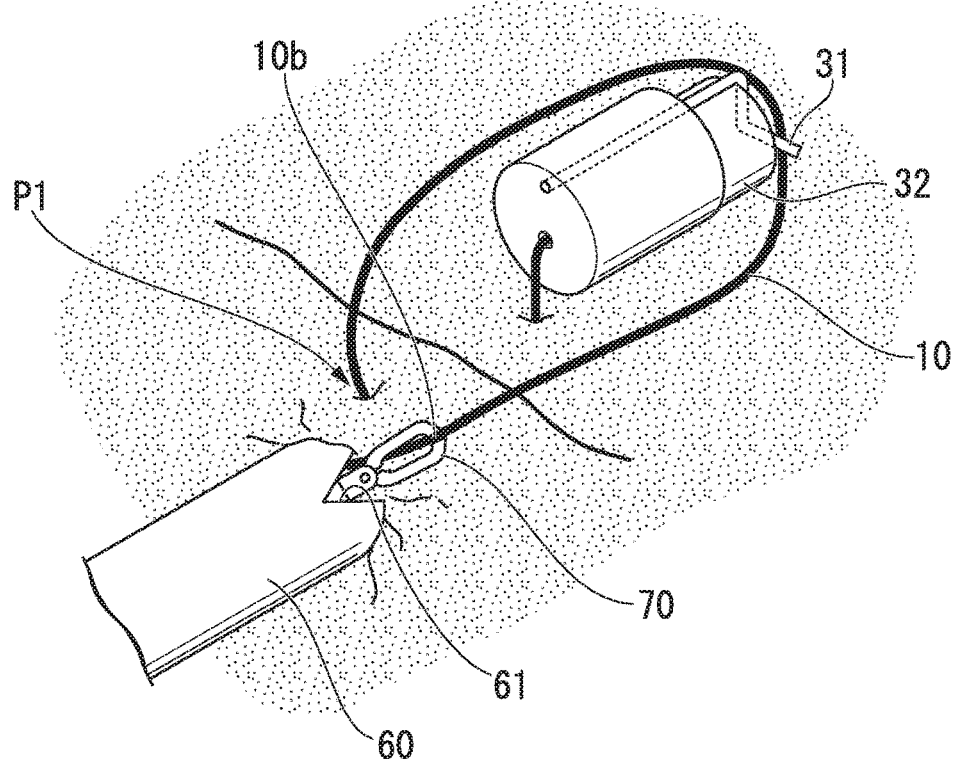
FIG. 5 is a view showing an operation when using the suture system including the suture body according to the first embodiment of the present invention.

Subsequently, the surgeon inserts a commonly-known grasping forceps into the sheath 60, and grips the second end 10b of the suture thread 10 at the tip portion of the grasping forceps 70 protruded from the sheath 60. As shown in FIG. 4, the surgeon operates the grasping forceps 70 to hook the suture thread 10 on the protruding portion 31. As shown in FIG. 5, the tip of the sheath 60 is pressed against the puncture point P1 where the suture thread 10 placed on the tissue comes out from the tissue, so that the notch 61 is close to the position of and the puncture point P1.

Figure 6:
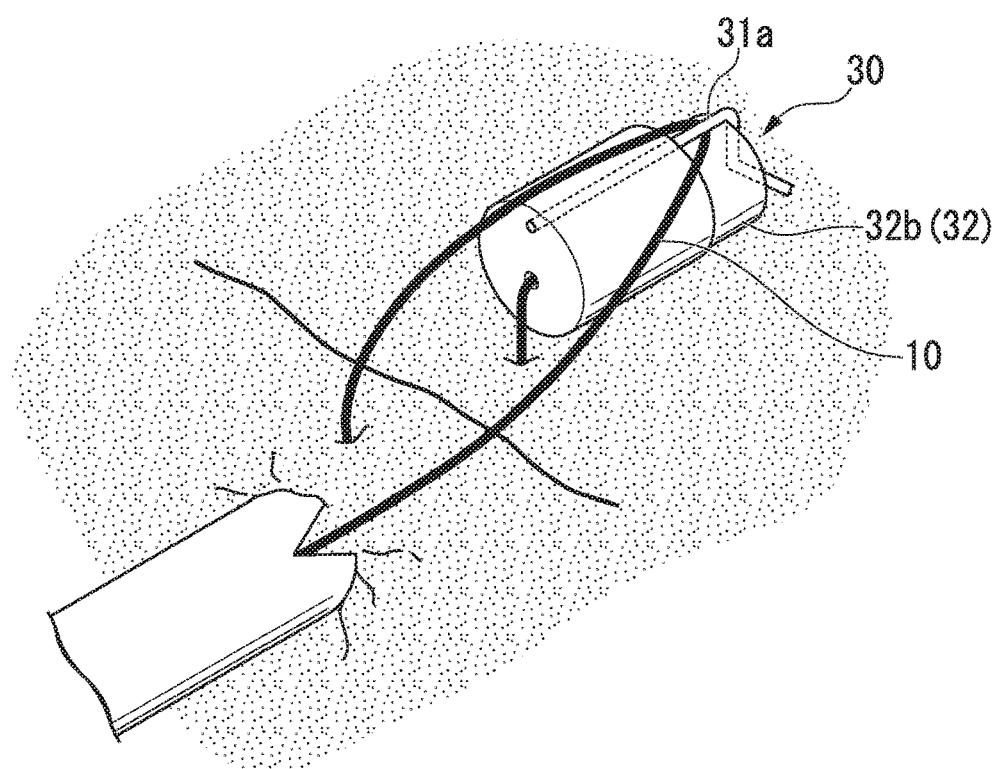
FIG. 6 is a view showing an operation when using the suture system including the suture body according to the first embodiment of the present invention.

In this state, when the surgeon retracts the grasping forceps 70, the grasping forceps 70 holding the suture thread 10 is drawn into the sheath 60 together with the suture thread 10 from the notch 61. The pulled suture 10 is brought into close contact with the outer peripheral surface of the protruding portion 31, and then elastically deforms the elastic member 32 to enter between the elastic member 32 and the protruding portion 31. As a result, the suture thread 10 receives a constant pressure between the first region 31a and the outer circumferential surface 32b and is frictionally engaged, so that the suture thread is fixed to the thread fixing member 30 as shown in FIG. 6 (thread fixing process). When it is desired to more strongly fix the suture thread 10, if the grasping forceps 70 and the second end 10b are moved to the outside of the sheath 60 and the thread fixing process is performed a plurality of times, the contact area between the suture thread 10 and the thread fixing member 30 so that the fixing force can be increased. The suture thread 10 may be hooked on the protruding portion 31 by operating the sheath 60 without releasing the grasping forceps 70 holding the suture thread 10 from the sheath 60 when the second or subsequent thread fixing process is performed.

When the thread fixing process is completed, extra suture thread 10 is cut off. When the cut suture 10 and suture needle 20 are retrieved, a series of suturing procedures is completed.

As described above, according to the suture body 1 and the suture system 100 of the present embodiment, the thread fixing member 30 includes the protruding portion 31 and the elastic member 32 which makes contact with the protruding portion 31 with a predetermined contact pressure. Therefore, by merely pulling the suture thread 10 around the protruding portion 31 and pulling the suture thread, it is possible to easily move the suture thread 10 between the protruding portion 31 and the elastic member 32 to fix the suture thread 10 and the thread fixing member 30. As a result, even if the grasping forceps 70 or the like introduced via the flexible endoscope 50 is used, a process corresponding to knot formation in the suturing treatment can be performed by a simple operation such as advancing and retracting. Therefore, according to the suture body 1 and the suture system 100 of the present embodiment, suturing can be easily performed without requiring the surgeon to acquire high-level techniques, and the suture body and the suture system of the present embodiment have excellent versatility.

In addition, since the protruding portion 31 is in contact with the elastic member 32 on the two surfaces of the outer peripheral surface 32b and the front end surface 32c orthogonal to the outer peripheral surface 32b, it is difficult for the suture thread 10, which is held between the outer peripheral surface 32b and the protruding portion 31, to come off from the suture fixing portion 30. Therefore, the fixed state of the suture thread can be stably maintained.

Since the fixing force of the suture thread 10 can be easily increased or decreased by changing the number of times of the thread fixing process, it is possible to easily perform suturing that exerts a suitable fixing force according to the thickness, hardness or the like of the object part, that is, for example, winding three times in suturing the large intestine, winding five times in the full layer suture of the stomach wall, or the like.

Since the protruding portion 31 is arranged within the range of the outer diameter of the base body 33 so as not to protrude radially outwardly of the base body 33, the protruding portion 31 is not caught when entering the channel of the endoscope 50.

Since the suture system 100 is provided with the sheath 60 having the notch 61, the grasping forceps 70 holding the suture thread 10 can be moved into the sheath 60 from the notch 61 while the state where the sheath 60 is pressed against the puncture point P1 is maintained. Therefore, it is possible to stably perform the thread fixing process.

In the present embodiment, the example in which the second end 10b of the suture thread 10 is bonded and fixed in the base 33 has been described, but the manner of fixing the suture thread to the thread fixing member is not limited thereto. For example, the second end 10b may be fixed while being sandwiched between the base 33 and the elastic member 32.

Figure 7:
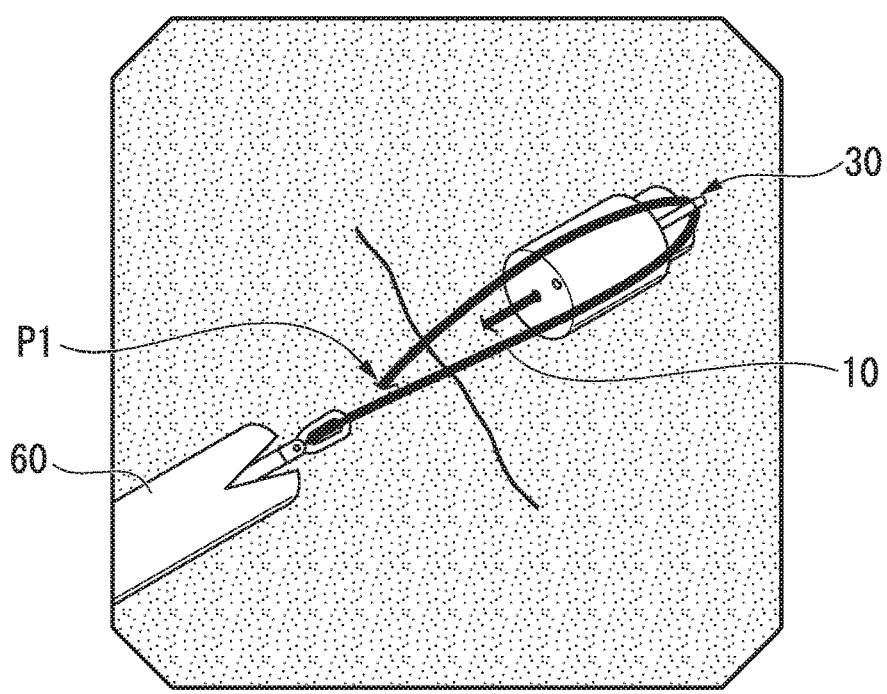
FIG. 7 is a view showing an example of a preferable positional relationship in a suture fixing step.

When performing the thread fixing process using the suture system 100 of the present embodiment, as shown in FIG. 7, in the field of view of the endoscope 50, if most of the thread fixing member 30 is located on the rear side of the puncture point P1 (the side away from the endoscope 50) and the suture thread 10 is pulled in a state where the direction in which the sheath 60 extends and the axial direction of the thread fixing member 30 substantially coincide with each other, that is, the thread fixing member 30 is positioned on the extension line of the sheath 60, it is possible to suitably wind the suture thread 10 around the thread fixing member 30 while limiting the rotation or the like of the thread fixing member 30.

Figure 9:
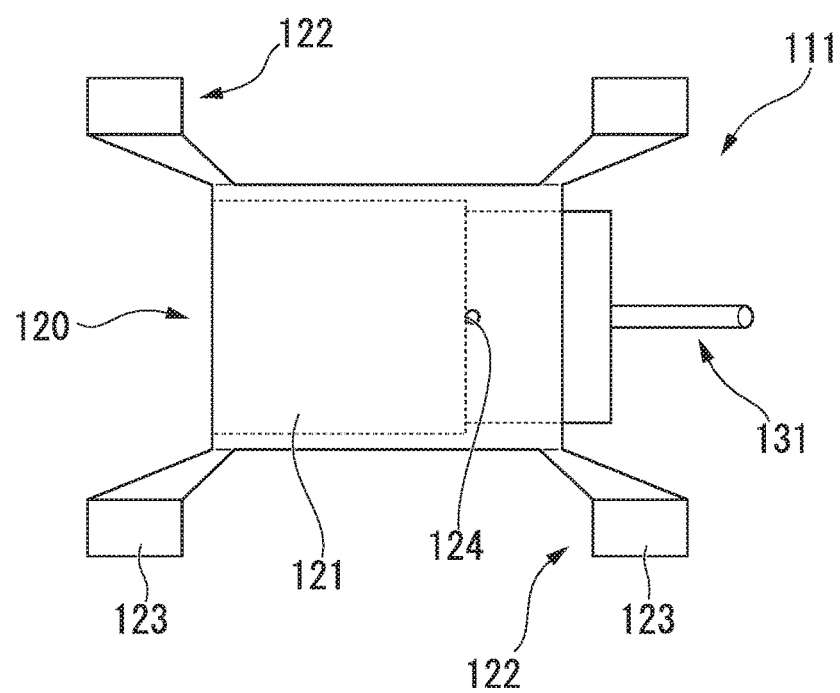
FIG. 9 is a view of the suture body according to the second embodiment of the present invention as seen from the bottom surface side.
Figure 10:
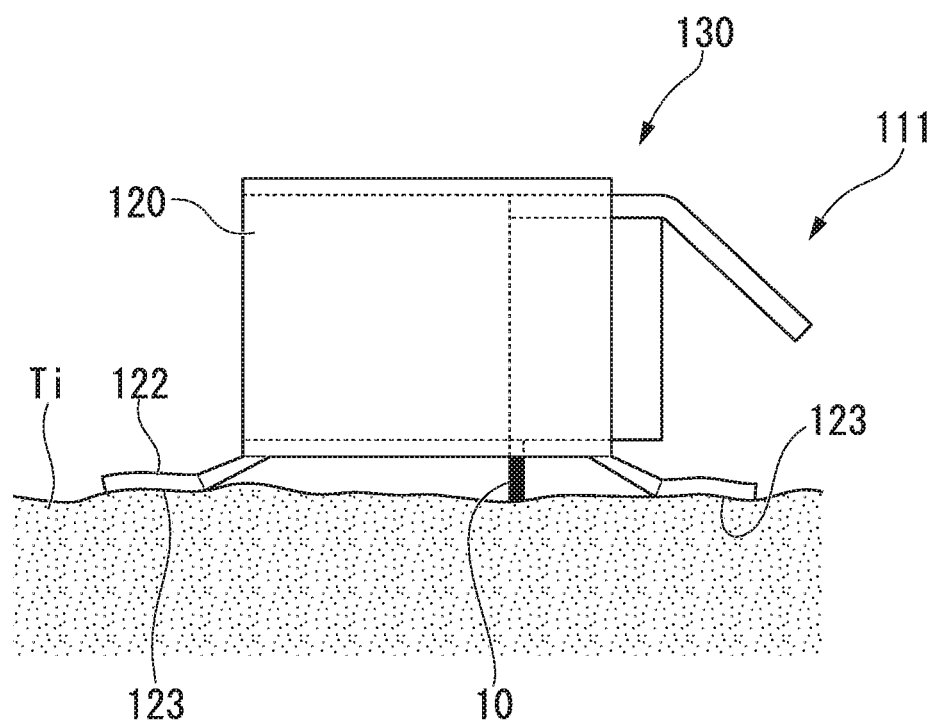
FIG. 10 is a view showing an operation when using the suture body according to the second embodiment of the present invention.

Next, a second embodiment of the present invention will be described with reference to FIGS. 8 to 10. In this embodiment, another form of the suture body will be described. In the following description, the same reference numerals are given to the configurations common to those already described, and redundant descriptions are omitted.

Figure 8:
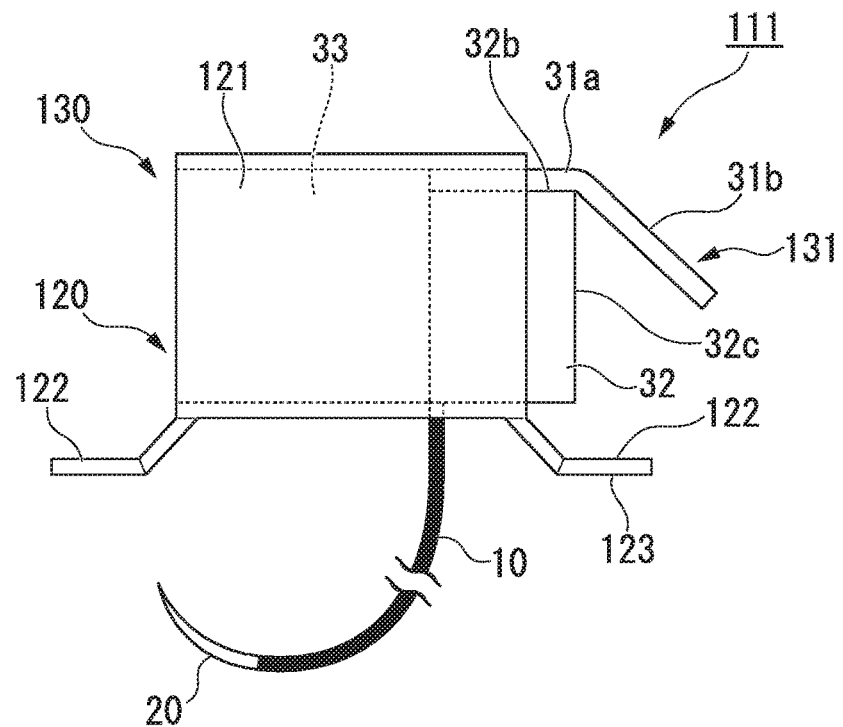
FIG. 8 is a right side view showing a suture body according to a second embodiment of the present invention.

FIG. 8 is a side view showing the suture body 111 of the present embodiment. FIG. 9 is a bottom view of the suture body 111. In FIG. 9, the suture thread 10 and the suture needle 20 are omitted for clarity.

The thread fixing member 130 of the suture body 111 includes a stabilizer 120 having four leg portions 122.

The stabilizer 120 has a cylindrical main body 121 and four leg portions 122 connected to the main body 121. Both of the main body 121 and the leg portion 122 are formed of a flexible material such as silicone, thin plate metal, or the like. The stabilizer 120 can be formed, for example, by processing a silicone tube or the like.

The stabilizer 120 is fixed to the base body 33 and the elastic member 32 so that all of the base body 33 and a part of the elastic member 32 are located inside the main body 121.

Each leg portion 122 extends to the lower side of the suture body 111 that is the side opposite to the upper side where the protruding portion 131 is arranged. A flat ground contact surface 123 is formed at an end portion of each leg portion 122 that extends to the lower side.

The suture thread 10 is connected to the base body 33 and the elastic member 32 in a state where the second end 10b (not shown) is sandwiched between the base body 33 and the elastic member 32. The suture thread 10 passes through a thread hole 124 formed in the main body 121 of the stabilizer 120 and extends to the lower side of the suture body 111.

The protruding portion 131 of the suture body 111 is different from the protruding portion 31 of the first embodiment in that it does not have the intermediate portion 31c and the first region 31a and the second region 31b are directly connected. As a result, the protruding portion 131 is exclusively in contact with the elastic member 32 on the outer circumferential surface 32b, and is slightly in contact with the distal end surface 32c.

The operation at the time of using the suture body 111 will be described. When the suture needle 20 is inserted into the target portion and the suture thread 10 is hooked on the tissue, the thread fixing member 130 approaches the tissue from the lower side where the suture thread 10 extends, and as shown in FIG. 10, the lower side of the thread fixing member 130 comes into contact with the tissue Ti.

At this time, the leg portion 122 provided on the stabilizer 120 comes into contact with the tissue Ti at the ground contact surface 123. As a result, the contact area between the thread fixing member 130 and the tissue Ti is increased, which contributes to the improvement of the stability of the thread fixing member 130 on the tissue Ti.

The thread fixing process can be performed in substantially the same manner as in the first embodiment. When the sheath 60 is pressed against the tissue Ti at the time of performing the suture fixing process, if the leg portion 122 extending to the proximal end side is sandwiched between the sheath 60 and the tissue Ti, the thread fixing member 130 is more stabilized.

In the suture body 111 of the present embodiment, like the suture body 1 of the first embodiment, it is possible to perform a process corresponding to knot formation in suturing treatment by a simple operation.

Since the stabilizer 120 having the leg portion 122 is provided, movement such as rotation of the thread fixing member 130 around the suture thread 10 or movement such as rotation of the thread fixing member 130 around the axis of the base member 33 and the elastic member 32 is suppressed during the thread hooking process and the thread fixing process. As a result, the thread hooking process can be performed more easily.

Since the leg portion 122 is formed of a flexible material, when the suture body 111 is inserted into the channel of the endoscope 50, the leg portion 122 can be easily deformed substantially parallel to the main body 121 and introduced into the channel, and after going out of the channel, the leg portion 122 can protrude to the lower side of the thread fixing member 130. Since the ground contact surface 123 can be deformed following the irregular surface shape of the tissue Ti, it is possible to stably obtain the effect of increasing the contact area.

Since the suture thread 10 is pulled out to the lower side of the thread fixing member 130, the thread fixing member 130 can be brought into contact with the tissue Ti in a state where the protruding portion 131 is reliably positioned on the side far from the tissue Ti. Therefore, it is possible to reduce the necessity of adjusting the orientation of the thread fixing member before the thread fixing process, and it is possible to smoothly perform the procedure.

In the present embodiment, the number of the leg portions provided on the stabilizer is not limited to four, but from the viewpoint of improving the stability of the thread fixing member, it is preferable that three or more leg portions are provided.

The leg portions are not limited to those having a ground contact surface. For example, it is possible to have a structure in which a protruding portion is provided instead of the ground contact surface, and the protruding portion is embedded in the tissue when the thread fixing member comes into contact with the tissue, thereby improving the stability.

When the suture thread 10 is pulled out by forming the thread hole 124 at the position in the center of gravity of polygonal whose apexes are at the positions of the plurality of leg portions 122 as the bottom view of the thread fixing member 130, the influence of the tension acting on the suture thread 10 on the orientation or direction of the thread fixing member 130 is reduced. As a result, it is possible to further stabilize the behavior of the thread fixing member 130 after coming into contact with the tissue Ti.

Although the embodiments of the present invention have been described above, the technical scope of the present invention is not limited to the above-described embodiments, and various combinations of constituent elements may be changed without departing from the spirit of the present invention, and it is possible to make various changes or delete them.

For example, in the suture body of the present invention, the base body is not essential. Therefore, the protruding portion and the suture thread may be directly fixed to the elastic member.

Instead of forming the thread fixing member in a substantially columnar shape, a part of the outer peripheral surface of the cylinder may be cut off in parallel with the axis. In this case, since the sectional shape orthogonal to the axis line of the thread fixing member is substantially D-shaped, the behavior of the thread fixing member can be stabilized by bringing the flat portion into contact with the tissue. It is also possible to further stabilize the behavior of the thread fixing member by connecting the suture thread with the thread fixing member so that the suture thread extends from the flat portion.

In the above-described embodiment, an example of a procedure corresponding to a single ligation in which a suture thread is held after passing through the tissue once has been described, but in the suture body of the present invention, by appropriately setting the length of the suture, continuous suturing in which the suture thread is made to pass through the tissue multiple times is also possible.

What is claimed is:

1. A suture body comprising:
    a suture thread that has a first end and a second end, and is configured to be fixed to a living tissue;
    a suture needle that is connected to the first end; and
    a thread fixing member that is connected to the second end, wherein the thread fixing member includes:
        a rod-shaped protruding portion; and
        a cylindrical-shaped elastic member that has an outer circumferential surface and is arranged so that the rod-shaped protruding portion is in direct contact with the outer circumferential surface of the elastic member at a predetermined contact pressure,
    the suture body is configured to receive the suture thread between the protruding portion and the elastic member by elastically deforming the elastic member, and hold the suture thread in place between the protruding portion and the elastic member,
    the suture body further includes a base body to which the protruding portion and the elastic member are fixed, and
    a part of the protruding portion is disposed within the base body.

2. The suture body according to claim 1, wherein the protruding portion is in contact with two or more surfaces of the elastic member at the contact pressure.

3. The suture body according to claim 1, wherein the suture thread extends in a lower side opposite to an upper side where the protruding portion is arranged in the thread fixing member.

4. The suture body according to claim 3, further comprising: a plurality of leg portions formed of a flexible material and extending in the lower side.

5. A suture system comprising:
    the suture body according to claim 1;
    an endoscope having a channel into which the suture body can be inserted; and
    a sheath configured to be inserted into the channel and having a notch at a distal end thereof.

6. The suture body according to claim 1, wherein an outer diameter of the base body is greater than an outer diameter of the elastic member, and the protruding portion is disposed within the outer diameter of the base body.

7. The suture body according to claim 1, wherein the suture thread extends from a first side of the suture body, and the rod-shaped protruding portion contacts the elastic member at a second side of the suture body, the second side being opposite to the first side.

8. The suture body according to claim 1, wherein the base body has a cylindrical shape.

9. The suture body according to claim 1, wherein the base body includes a through hole, and a portion of the rod-shaped protruding portion is disposed in the through hole.

10. The suture body according to claim 1, wherein the base body includes a through hole, and a portion of the suture thread is disposed in the through hole.

11. A suture body comprising:
    a base body;
    an elastic member attached to the base body;
    a rod-shaped protruding portion that is attached to the base body and is held in direct contact with an outer surface of the elastic member at a predetermined contact pressure; and
    a suture thread that is attached to the base body at one end and includes a suture needle disposed at a second end,
    wherein the elastic member and the protruding portion are each directly fixed to the base body, and wherein the suture body is configured to receive the suture thread between the protruding portion and the elastic member by elastically deforming the elastic member, and hold the suture thread in place between the protruding portion and the elastic member via friction, the suture thread being held without a knot.

12. A suture body comprising:
a suture thread that has a first end and a second end, and is configured to be fixed to a living tissue;
a suture needle that is connected to the first end; and
a thread fixing member that is connected to the second end,
wherein the thread fixing member includes:
a rod-shaped protruding portion; and
an elastic member that has an outer circumferential surface and is arranged so that the rod-shaped protruding portion is in direct contact with the outer surface of the elastic member at a predetermined contact pressure,
the suture body is configured to receive the suture thread between the protruding portion and the elastic member by elastically deforming the elastic member, and hold the suture thread in place between the protruding portion and the elastic member,
the suture body further includes a base body to which the protruding portion and the elastic member are directly fixed without moving with respect to the base body, and
a part of the protruding portion is disposed within the base body.

* * * * *